United States Patent
Ranish et al.

(10) Patent No.: US 9,140,647 B2
(45) Date of Patent: *Sep. 22, 2015

(54) TEST APPARATUS FOR REFLECTIVE CAVITY CHARACTERIZATION

(71) Applicant: Applied Materials, Inc., Santa Clara, CA (US)

(72) Inventors: Joseph M. Ranish, San Jose, CA (US); Joseph Johnson, Redwood City, CA (US); Mehran Behdjat, San Jose, CA (US)

(73) Assignee: APPLIED MATERIALS, INC., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/543,649

(22) Filed: Nov. 17, 2014

(65) Prior Publication Data

US 2015/0070686 A1    Mar. 12, 2015

Related U.S. Application Data

(63) Continuation of application No. 13/922,712, filed on Jun. 20, 2013, now Pat. No. 8,896,837.

(51) Int. Cl.
*G01N 21/55* (2014.01)
*G01N 21/47* (2006.01)

(52) U.S. Cl.
CPC .......... *G01N 21/55* (2013.01); *G01N 21/4738* (2013.01); *G01N 2201/08* (2013.01)

(58) Field of Classification Search
CPC .......... G02B 1/04; G02B 1/045; G02B 1/005; G02B 1/10; G02B 1/12; G02B 23/26; G02B 6/0006; G02B 6/0008; G02B 19/0019; G02B 19/0042; G02B 19/009; G02B 1/041; G02B 1/046; G02B 1/113; G02B 1/118
See application file for complete search history.

(56) References Cited

U.S. PATENT DOCUMENTS

| | | | |
|---|---|---|---|
| 3,506,359 A | 4/1970 | Burke, Jr. et al. | |
| 3,920,336 A | 11/1975 | Sackett | |
| 4,488,814 A | 12/1984 | Johnson | |
| 4,752,689 A | 6/1988 | Satake | |
| 4,868,383 A | 9/1989 | Kurtz et al. | |
| 5,251,004 A * | 10/1993 | Doiron et al. | 356/236 |
| 5,258,363 A * | 11/1993 | Hed | 505/160 |
| 5,308,965 A | 5/1994 | Wieloch | |
| 5,369,481 A | 11/1994 | Berg et al. | |
| 5,537,203 A | 7/1996 | Carr | |
| 8,277,048 B2 | 10/2012 | Artsyukhovich et al. | |
| 2012/0229801 A1 | 9/2012 | Park et al. | |

* cited by examiner

*Primary Examiner* — Michael P Stafira
(74) *Attorney, Agent, or Firm* — Patterson & Sheridan, LLP

(57) ABSTRACT

An apparatus for reflectivity measurement is provided. The apparatus generally measures reflectivity characteristics of a reflective surface, such as a reflective cavity of a light array. The apparatus generally comprises a body defining a volume and a light emitting element disposed outside the volume. A sensor coupled to the body detects light reflected from a reflective surface. Various embodiments provide positioning of the apparatus relative to a light array having a reflective cavity.

20 Claims, 3 Drawing Sheets

ABSTRACT

TEST APPARATUS FOR REFLECTIVE CAVITY CHARACTERIZATION

CROSS-REFERENCE TO RELATED APPLICATIONS

This application is a continuation of U.S. patent application Ser. No. 13/922,712, filed Jun. 20, 2013, which is incorporated herein by reference in its entirety.

BACKGROUND

1. Field

Embodiments provided herein generally relate to reflectivity metrology. More specifically, embodiments provided herein relate to a test apparatus for reflective cavity characterization.

2. Description of the Related Art

Thermal processing is commonly practiced in the semiconductor industry. Semiconductor substrates are subjected to thermal processing in the context of many transformations, including doping, activation, and annealing of gate, source, drain, and channel structures, siliciding, crystallization, oxidation, and the like. Techniques of thermal processing have progressed from simple furnace baking to various forms of increasingly rapid thermal processing such as spike annealing and laser annealing.

Rapid Thermal Processing (RTP) is a well-developed technology for fabricating semiconductor integrated circuits. RTP is a process in which the substrate is irradiated with high intensity optical radiation in an RTP chamber to quickly heat the substrate to a relatively high temperature to thermally activate a process in the substrate. Once the substrate has been thermally processed, the radiant energy is removed and the substrate cools. RTP is an energy efficient process because the chamber in which the RTP is performed is not heated to elevated temperature required to process the substrate. In an RTP process, only the substrate is heated. Thus, the processed substrate is not in thermal equilibrium with the surrounding environment, namely the chamber.

Although annealing in early stages substrate processing technology involved heating multiple substrate for long periods in an annealing oven, RTP has been increasingly used to satisfy ever more stringent requirements for processing substrates with increasingly smaller circuit features. RTP is typically performed in a single substrate chamber by irradiating a substrate with light from an array of high intensity lamps directed at the substrate. The radiation is at least partially absorbed by the substrate and quickly heats the substrate to a desired high temperature. The desired temperatures generally are above 600° C. and in certain applications, above 1000° C. The radiant heating can be quickly activated and deactivated to controllably heat the substrate over short time intervals, such as between about 60 seconds and about 1 second.

An array of high intensity lamps providing heat to the substrate may be designed in various manners to irradiate the substrate. Some arrays utilize reflective cavities having an electromagnetic radiation source disposed therein. The reflective cavities generally affect how the electromagnetic radiation is provided to the substrate, such as the total amount of light as well as the spatial and frequency distribution of the light. Thus, it is generally desirable to be able to measure the reflectivity of the reflective cavities. Integrating spheres are generally used to measure various spatially integrated qualities of electromagnetic radiation. While integrating spheres provide a convenient way to measure the total light released from a lamp reflector system, the measurement combines attributes of the lamp with those of the reflector. Moreover, many integrating spheres lack the capability of measuring reflectivity from a reflective cavity.

Therefore, what is needed in the art are apparatus for measuring reflectivity of reflective cavities, such as reflective cavities for an array of high intensity lamps for use in an RTP process.

SUMMARY

In one embodiment, an apparatus for measuring reflectivity is provided. The apparatus may include a body defining a volume and the body may have an opening. A stop may be disposed opposite the opening and an energy transmitting element may be coupled to and extend from the stop through the body and through the opening. A light emitting element may be coupled to the energy transmitting element and the light emitting element may be located outside the body. A light sensor may be coupled to the body and one or more support elements may be coupled to and extend from the body.

In another embodiment, an apparatus for measuring reflectivity is provided. The apparatus may include a body defining a volume and the body may have an opening. A stop may be disposed opposite the opening and an energy transmitting element may be coupled to and extend from the stop through the body and through the opening. A light emitting element may be coupled to the energy transmitting element and the light emitting element may be located outside the body. A light sensor may also be coupled to the body.

In yet another embodiment, an apparatus for measuring reflectivity is provided. The apparatus may include a spherical body having a flat bottom surface and the flat bottom surface may have an opening. An optical fiber may be coupled to a stop located opposite the opening and a light transmitting element having a reflective sheath may be coupled to and extend from the stop. The light transmitting element may extend through the spherical body and through the opening and a light emitting element may be coupled to the light transmitting element. The light emitting element may be located outside the spherical body, a light sensor may be coupled to the spherical body, and one or more support elements may be coupled to and extends from the spherical body.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Embodiments provided herein generally relate to reflectivity metrology. More specifically, embodiments provided herein relate to a test apparatus for reflective cavity characterization. The reflectivity test apparatus may be used to measure the reflectivity of reflective cavities in a light array for use in RTP processing. It should be known that the term "light" used herein may refer to electromagnetic radiation within the visible spectrum, but may also refer to infrared radiation and/or ultraviolet radiation.

Figure 1A:
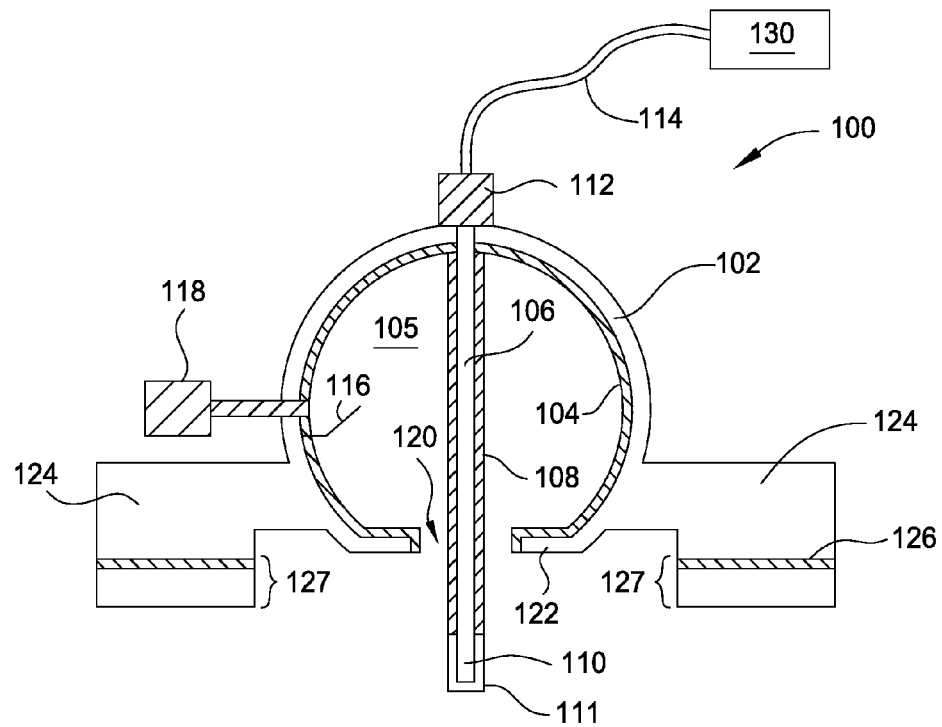
FIG. 1A is a cross-sectional view of a reflectivity measurement apparatus according to certain embodiments provided herein.

FIG. 1A is a cross-sectional view of a reflectivity measurement apparatus 100 according to one embodiment. The reflectivity measurement apparatus 100 has a body 102 coated with a reflective material 104 which may define a volume 105. An energy transmitting element 106 may extend from a stop 112 through the volume 105 beyond an opening 120. An energy source 130 may be coupled to the energy transmitting element 106 through the stop 112. A light emitting element 110 may be coupled to the energy transmitting element 106. A sensor 118 may also be coupled to the body 102. In addition, one or more support elements 124 may be coupled to the body 102.

The body 102 may be formed from a polymer material, such as various plastics or Teflon® polymer, which allow the body 102 to be formed into a desired shape. In one embodiment, the body 102 may be substantially spherical. The reflectivity measurement apparatus 100 may comprise an integrating sphere. A mating region 122 of the body 102 may be a substantially flat portion of the body 102 and may be adapted to abut a reflective cavity disposed in a member, such as a light array, coupled to the body 102 at the mating region 122. The mating region 122 may be a bottom portion of the body 102. The body 102 defining the volume 105 may have the opening 120 formed through the bottom portion of the body 102 and the opening 120 may have an outer diameter defined by the mating region 122. In certain embodiments, the body 102 may have a diameter between about 1 in and about 10 in, such as between about 3 in and about 5 in.

The body 102 may also be coated with the reflective material 104. In one embodiment, the reflective material 104 may be disposed on an interior surface of the body 102 adjacent the volume 105. In certain embodiments, the reflective material 104 may be a reflective liner, such as gold, aluminum, or a fluorocarbon polymer, such as a TEFLON® polymer, or the reflective material 104 may be a reflective coating, such as titanium oxide or barium sulfide. The reflective material 104 may be selected to reflect light provided to the volume 105. In one embodiment, the reflective material 104 may have a roughened surface to further increase the dispersion of the reflected light.

The energy transmitting element 106 may be coupled to the body 102 and extend from the stop 112 located opposite the opening 120. The energy transmitting element 106 may extend from the stop 112 through the opening 120. The stop 112 may also be adapted to adjust the length of the energy transmitting element 106 extending from the stop 112. Alternatively, the stop 112 may be positioned elsewhere in the body 102 with the energy transmitting element 106 being angled or bent so that the energy transmitting element 106 extends through the opening 120. In certain embodiments, the length of the energy transmitting element 106 which extends beyond the opening 120 may be up to a depth of a reflective cavity. For example, the length of the energy transmitting element 106 may be between about 12 mm and about 50 mm, such as about 25 mm. The light emitting element 110 may be coupled to the energy transmitting element 106 and may be located outside of the volume 105. In certain embodiments, the length of the light emitting element 110 may be between about 5 mm and about 20 mm, such as between about 10 mm and about 15 mm, such about 13 mm.

In one embodiment, the energy transmitting element 106 may transmit electrical energy from the energy source 130 to the light emitting element 110. In this embodiment, the energy transmitting element 106 may comprise a polymer material, such as DELRIN® polymer, having electrically conductive wires contained therein and the light emitting element 110 may be a light bulb or the like. In another embodiment, the energy transmitting element 106 may transmit light provided by the energy source 130 to the light emitting element 110. For example, the energy transmitting element 106 may comprise a substantially transparent rod or fiber, such as a quartz, plastic, or glass rod, adapted to transfer light to the light emitting element 110. The light emitting element 110 may be a part of or integral to the substantially transparent rod. Light may travel within the rod to the light emitting element 110 where the light may be emitted. In certain embodiments, the light emitting element 110 may comprise a fiber having a roughened end which may function as a light emitting origin.

The energy transmitting element 106 may be encased in a sheath 108. The sheath 108 may be a reflective material such as gold, aluminum, or Teflon® polymer. The sheath 108 may reflect light within the energy transmitting element 106 to transfer the light to the light emitting element 110. The sheath 108 may encase the energy transmitting element 106 and extend a distance along the energy transmitting element 106 beyond the volume 105. In addition, the sheath 108 may increase the amount of light reflected within the volume 105.

In one embodiment, the sheath 108 may encase a portion of the energy transmitting element 106. In this embodiment, the portion of the energy transmitting element 106 exposed may be the light emitting element 110. The portion of the light emitting element 110 exposed may be covered by a cap 111, such as a light diffuser. The cap 111 may be substantially translucent and allow light provided by the light emitting element 100 to emit diffuse light. In one embodiment, the cap 111 may comprise frosted glass. In another embodiment, the cap 111 may be formed from a reflective material.

Energy is generally provided to the light emitting element 100 via the energy transmitting element 106 from the energy source 130. The energy source 130 may be adapted to provide electrical energy or light. The energy source 130 may be coupled to the energy transmitting element 106 via a cable 114 which may be coupled to the body 102 by the stop 112. In embodiments utilizing a light bulb as the light emitting element 110, the energy source 130 may provide electrical energy to the light emitting element 110 via the cable 114 and the energy transmitting element 106. In embodiments where the light emitting element 110 is a portion of the quartz rod, the energy source 130 provides light via the cable 114, which may be an optical fiber, to the stop 112. The stop 112 may have a lens disposed therein that focuses the light provided by the cable 114 onto the energy transmitting element 106. The light then travels within the energy transmitting element 106 encased in the sheath 108 to the light emitting element 110.

The sensor 118 coupled to the body 102 may be a light sensor. The sensor 118 may be coupled to the body 102 at any convenient location and may be located on the body 102 to avoid a direct line of sight to the light emitting element 110. A baffle 116 may also be coupled to the body 102. The baffle 116 may be coupled to the body 102 at a location between the sensor 118 and the light emitting element 110. For example, the baffle 116 may be located along a direct optical path between an entry point of the sensor 118 at the reflective material 104 of the body 102 and the light emitting element 110. The baffle 116 may prevent light emitted from the light emitting element 110 from directly illuminating the sensor 118. The baffle 116 may be made from a substantially opaque material or a reflective material. The sensor 118 may be adapted to measure the reflectivity characteristics of a reflective cavity. In one embodiment, the sensor 118 may be a spectrophotometer.

The sensor 118 may be adapted to detect wavelengths of light that for determining the reflectivity or reflective characteristics of a reflective surface. The sensor 118 may be a photodiode, a photodiode array, a CCD matrix, a camera, or other photoelectric device of photosensitive element. For example, the sensor 118 may comprise a semi-conductive material, such as silicon or InGaAs. In one embodiment, the sensor 118 may be adapted to detect wavelengths of light between about 400 nm and about 4,000 nm, such as between about 700 nm and about 2,000 nm, such as about 900 nm.

The one or more support elements 124 may be coupled to and extend from the body 102. Similar to the body 102, the one or more support elements may be made from a polymer material, such as various plastics or Teflon® polymer. The one or more support elements 124 extend laterally outward from the body 102 and comprise a positioning region 127 which may be inserted into cavities adjacent the reflective cavity being analyzed. As such, the one or more support elements 124 may be adapted to conform to the cavity arrangement of a light array. For example, the one or more support elements 124 may oppose one another at a 180° or they may form other various angles to adapt to a light array. A positioning portion 127 of the one or more support elements 124 may be disposed in the adjacent cavities to ensure proper positioning of the reflectivity measurement apparatus 100. The positioning portion 127 may be substantially columnar and may be adapted to meet the tolerances of the cavities within which the positioning portion 127 may be disposed. A seating element 126, such as an O-ring, may circumscribe the positioning portion 127. The seating element 126 may comprise an elastomeric material and may provide firm seating of the positioning portion 127 within the adjacent cavities.

Figure 1B:
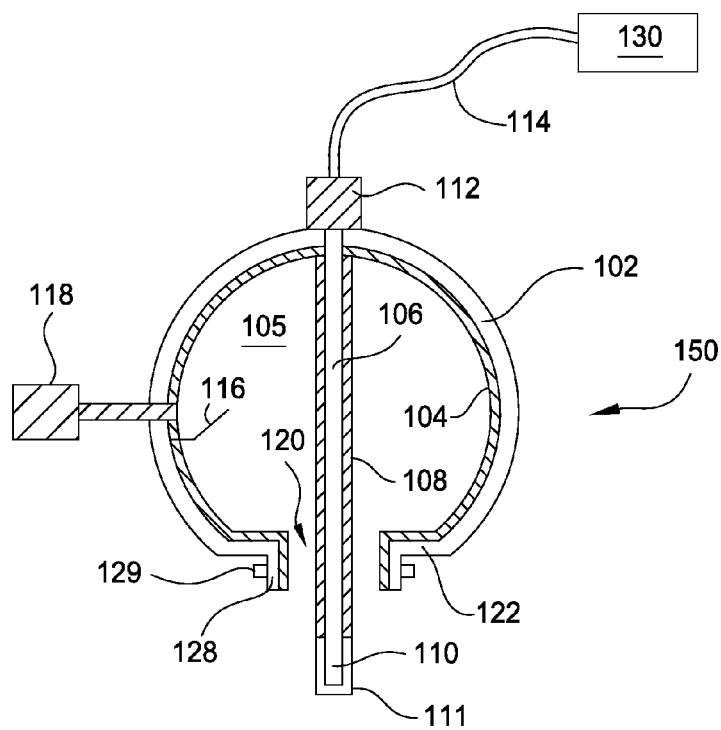
FIG. 1B is a cross-sectional view of a reflectivity measurement apparatus according to certain embodiments provided herein.

FIG. 1B is a cross-sectional view of a reflectivity measurement apparatus 150 according to certain embodiments provided herein. Identical features of the reflectivity measurement apparatus 150 described with regard to FIG. 1A will not be further discussed for the sake of brevity. The mating region 122 of the body 102 may be adapted to abut a reflectivity cavity to be analyzed. The flat portion of the mating region 122 may be disposed adjacent a body of a light array and a positioning element 128 may extend from the mating region 122. The positioning element 128 may be formed from the same materials as the body 102 and may extend downward from the mating region 122. The positioning element 128 may be substantially ring-like and comprise an outer diameter similar to a diameter of a cavity to be analyzed. The ring-like positioning element 128 may be a continuous ring or a non-continuous ring. Referring back to FIG. 1A, the positioning portion 127 of the one or more support elements 124 in the apparatus of FIG. 1A may utilize an element similar to the positioning element 128. Thus, the positioning portion 127 may be substantially ring-like and may be a continuous or non-continuous ring-like structure.

A seating element 129, such as an O-ring, may circumscribe the positioning element 128. The seating element 129 may comprise an elastomeric material and may provide firm seating of the positioning element 128 within cavity being analyzed. When the reflectivity measurement apparatus 150 is positioned relative to the cavity to be analyzed, the positioning element 128 may extend a distance into the cavity 128 sufficient to prevent the reflectivity measurement apparatus 150 from moving during analysis of the cavity. In one embodiment, the energy transmitting element 106 may extend beyond the positioning element 128

Figure 1C:
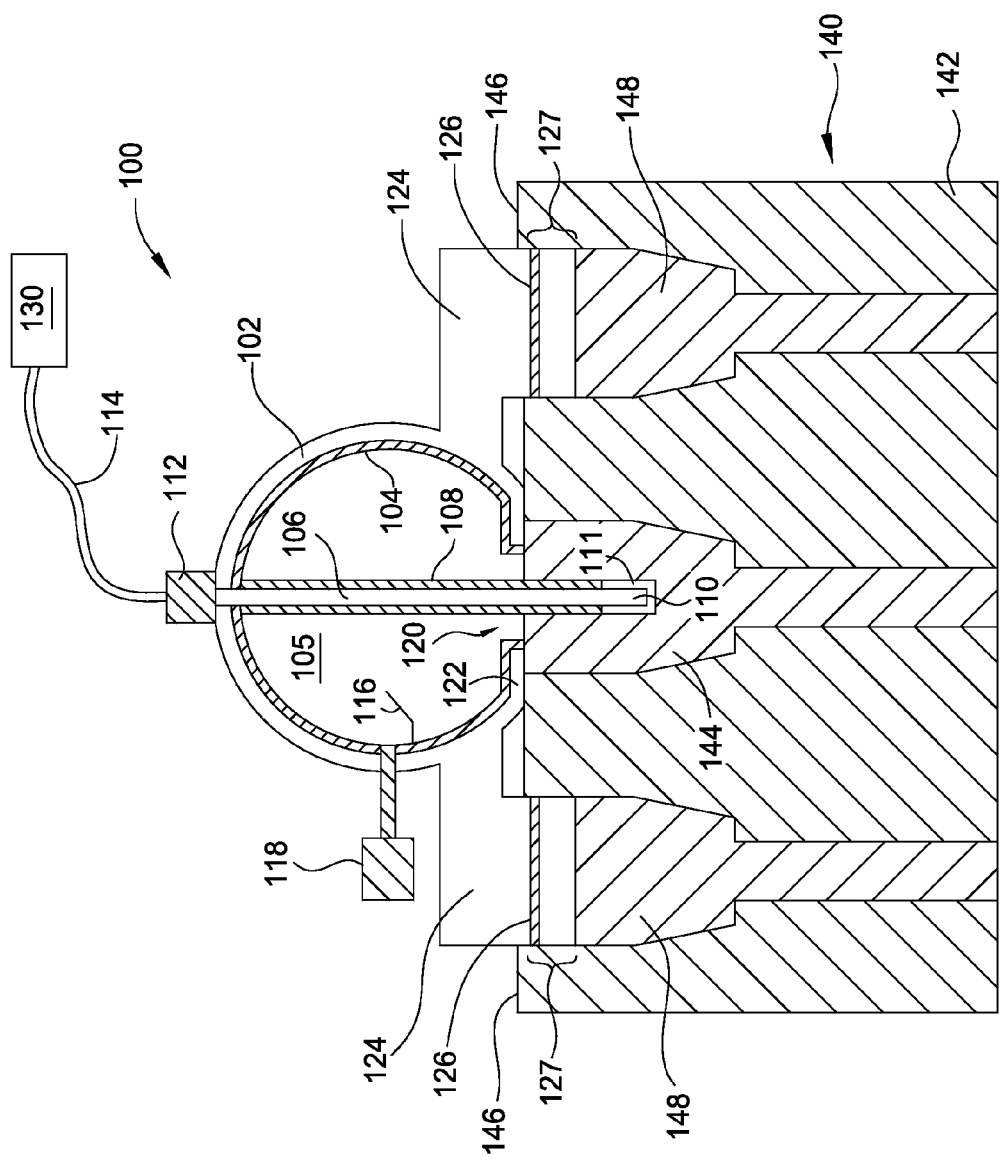
FIG. 1C is a cross-sectional view of a reflectivity measurement apparatus and a portion of a lighting array according to certain embodiments provided herein.

FIG. 1C is a cross-sectional view of a reflectivity measurement apparatus and a portion of a light array 140 according to certain embodiments provided herein. Identical features of the reflectivity measurement apparatus 100 described with regard to FIG. 1A will not be further discussed for the sake of brevity. The light array 140 may comprise a body 142 having a plurality of reflective cavities 144 disposed therein. The light array 140 may used for heating a substrate, such as heating a semi-conductive substrate during an RTP process. An interior surface of the reflective cavities 144 may be coated with a reflective material by an electroplating or other similar process. Although generally cylindrical in shape, the reflective cavities 144 may comprise other shapes. A light source, such as a high intensity light emitting filament, may be disposed within the reflective cavity 144. As previously described, the reflectivity measurement apparatus 100 may be used to the measure the reflectivity of the reflective cavity 144. Determining the reflectivity of the reflective cavities 144 is useful for determining if any defects exist in the reflective cavity which may affect the heating profile provided to a substrate by the light array 140.

The reflectivity measurement apparatus 100 may be placed adjacent a top surface 146 of the reflective cavity 144 to be analyzed. The mating region 122 rests on the top surface 146 and the one or more support elements 124 secure the reflectivity measurement apparatus 100 in place by anchoring the positioning portion 127 within adjacent cavities 148. The seating element 126 may prevent lateral movement of the positioning portion 127 when disposed in the adjacent cavities 148.

The energy transmitting element 106 extends from the stop 112 which may be located on the body 102 opposite the opening 120. The energy transmitting element 106 extends from the stop 112 through the opening 120 and into the reflective cavity 144. The light emitting element 110 coupled to the energy transmitting element 106 is positioned to simulate the light emitting filament which is present in the light array 140 during operation. As such, the light emitting filament of the light array 140 may be removed during use of the apparatus 100.

Light from the light emitting element 110 is generally reflected by the reflective coating of the reflective cavity 144 into the volume 105 of the apparatus 100. The diffuse light emitted by the light emitting element 110 is selected to mimic light provided by the light emitting filament of the light array 140. The sensor 118 detects the reflected light and provides feedback concerning the reflective characteristics of the reflective cavity 144. If a defect in the reflectivity cavity 144 is found, the reflective cavity 144 may be repaired to improve the reflectivity of the reflective cavity 144.

Figure 2:
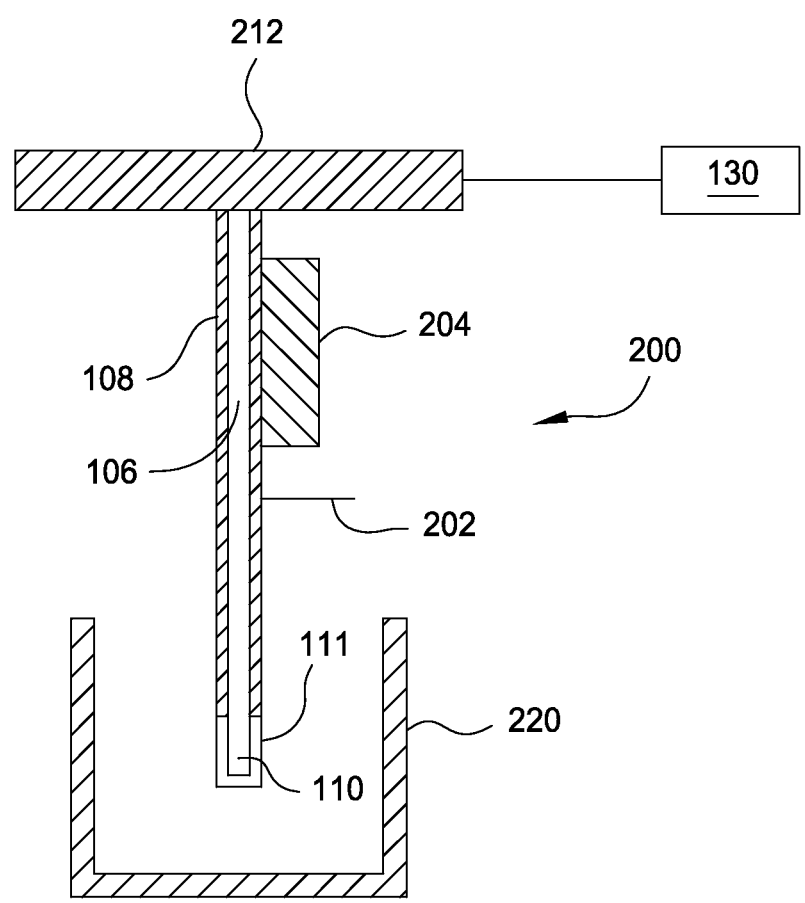
FIG. 2 is a schematic, cross-sectional view of a reflectivity measurement apparatus according to certain embodiments provided herein.

FIG. 2 is a schematic, cross-sectional view of a reflectivity measurement apparatus 200 according to certain embodiments provided herein. Identical features of the reflectivity measurement apparatus 100 described with regard to FIG. 1A will not be further discussed for the sake of brevity. The apparatus 200 comprises a frame element 212 having the energy transmitting element 106 extending therefrom. The light emitting element 100 may be coupled to the energy transmitting element 106. The apparatus 200 may be positioned such that the light emitting element 110 is disposed within a reflective cavity 220 to simulate a light emitting filament present in the reflective cavity 220 during an RTP process. The frame element 212 is generally coupled to the energy source and provides electrical energy or light to the energy transmitting element 106. The frame element 212 may be coupled to a wall or ceiling of an RTP chamber, may be freestanding to position the apparatus 200 for analyzing a reflective cavity 220, or may be attached to a robot arm for automated measurements of a reflective cavity 220 in a light array.

A sensor 204 coupled to the energy transmitting element 106 may be a light sensor. The sensor 204 may be coupled to the energy transmitting element 106 at any location outside the reflective cavity 220 being illuminated by the light emitting element 110 or the sensor 204 may be coupled to the frame element 212. In certain embodiments, multiple sensors 204 may be used to provide additional measurements for determining angular information. The sensor 204 may be adapted to measure the reflectivity characteristics of a reflective cavity 220. In one embodiment, the sensor 204 may be a spectrophotometer.

An optional baffle 202 may also be coupled to the energy transmitting element 106. The optional baffle 202 may be coupled to the energy transmitting element 106 at a location between the sensor 204 and the light emitting element 110. The optional baffle 202 may prevent light emitted from the light emitting element 110 from directly illuminating the sensor 204, thus the optional baffle 202 may prevent line of sight illumination of the sensor 204. The optional baffle 202 may be made from a substantially opaque material or a reflective material. In certain embodiments, the optional baffle 202 may not be present in the apparatus 200. In embodiments without the optional baffle 202, an out of reflective cavity 220 measurement may be used to obtain a direct light measurement which may be subtracted from an in reflective cavity 220 measurement. The apparatus 200 may be used to obtain an angular distribution measurement with multiply spaced sensors 204, which may be useful in determining the individual contribution of geometry, roughness, and reflectivity of the reflective cavity 220.

The sensor 204 may be adapted to detect wavelengths of light that for determining the reflectivity or reflective characteristics of a reflective surface. In one embodiment, the sensor 204 may comprise a semi-conductive material, such as silicon or InGaAs. In one embodiment, the sensor 204 may be adapted to detect wavelengths of light between about 400 nm and about 4,000 nm, such as between about 700 nm and about 2,000 nm, such as about 900 nm.

While the foregoing is directed to embodiments of the present disclosure, other and further embodiments of the disclosure may be devised without departing from the basic scope thereof, and the scope thereof is determined by the claims that follow.

The invention claimed is:

1. An apparatus for measuring reflectivity, comprising:
a body defining a volume, the body having an opening;
a stop disposed opposite the opening;
an energy transmitting element coupled to and extending from the stop, the energy transmitting element extending through the body and through the opening;
a light emitting element coupled to the energy transmitting element, the light emitting element located outside the body;
a light sensor coupled to the body; and
one or more support elements coupled to and extending from the body.

2. The apparatus of claim 1, further comprising a baffle coupled to an interior surface of the body.

3. The apparatus of claim 1, wherein the body further comprises a reflective lining.

4. The apparatus of claim 1, wherein the energy transmitting element comprises a quartz rod.

5. The apparatus of claim 4, wherein a reflective sheath surrounds the quartz rod.

6. The apparatus of claim 5, wherein the reflective sheath comprises aluminum or a fluorocarbon polymer.

7. The apparatus of claim 1, wherein the light emitting element is disposed substantially within a reflective cavity of a member coupled to the opening of the body.

8. The apparatus of claim 7, wherein the light emitting element is a diffuse light source.

9. The apparatus of claim 1, wherein the light sensor detects reflected light having a wavelength from about 400 nm to about 4000 nm.

10. The apparatus of claim 1, wherein the body is substantially spherical.

11. The apparatus of claim 1, wherein the one or more support elements position the body relative to a reflective surface.

12. The apparatus of claim 11, wherein the one or more support elements further comprise compression O-rings.

13. The apparatus of claim 1, wherein the stop is coupled to the body.

14. An apparatus for measuring reflectivity, comprising:
a body defining a volume, the body having an opening;
a stop disposed opposite the opening;
an energy transmitting element coupled to and extending from the stop, the energy transmitting element extending through the body and through the opening;
a light emitting element coupled to the energy transmitting element, the light emitting element located outside the body; and
a light sensor coupled to the body.

15. The apparatus of claim 14, further comprising:
one or more support elements coupled to and extending from the body.

16. The apparatus of claim 14, wherein the stop is coupled to the body.

17. An apparatus for measuring reflectivity, comprising:
a spherical body having a flat bottom surface, the flat bottom surface having an opening;
an optical fiber coupled to a stop located opposite the opening;
a light transmitting element having a reflective sheath coupled to and extending from the stop, the light transmitting element extending through the spherical body and through the opening;
a light emitting element coupled to the light transmitting element, the light emitting element located outside the spherical body;
a light sensor coupled to the spherical body; and
one or more support elements coupled to and extending from the spherical body.

18. The apparatus of claim 17, further comprising a baffle coupled to an interior surface of the spherical body.

19. The apparatus of claim 17, wherein the spherical body further comprises a reflective lining.

20. The apparatus of claim 17, wherein the light transmitting element comprises a quartz rod and the reflective sheath comprises aluminum or a fluorocarbon polymer.

\* \* \* \* \*